United States Patent
Angelides

(10) Patent No.: US 8,066,640 B2
(45) Date of Patent: Nov. 29, 2011

(54) CELLULAR GPRS-COMMUNICATION LINKED GLUCOMETER—PEDOMETER

(75) Inventor: Kimon Angelides, Houston, TX (US)

(73) Assignee: EOS Health, Inc., Houston, TX (US)

(*) Notice: Subject to any disclaimer, the term of this patent is extended or adjusted under 35 U.S.C. 154(b) by 49 days.

(21) Appl. No.: 12/426,984

(22) Filed: Apr. 21, 2009

(65) Prior Publication Data

US 2009/0264337 A1  Oct. 22, 2009

Related U.S. Application Data

(60) Provisional application No. 61/046,881, filed on Apr. 22, 2008.

(51) Int. Cl.
*A61B 5/00* (2006.01)
(52) U.S. Cl. ........... 600/301; 600/300; 600/365; 435/14
(58) Field of Classification Search .................. None
See application file for complete search history.

(56) References Cited

U.S. PATENT DOCUMENTS

| | | | | |
|---|---|---|---|---|
| 7,161,484 B2* | 1/2007 | Tsoukalis | ............... | 340/539.12 |
| 2003/0208113 A1* | 11/2003 | Mault et al. | ................... | 600/316 |
| 2004/0133079 A1* | 7/2004 | Mazar et al. | .................. | 600/300 |
| 2005/0080322 A1* | 4/2005 | Korman | ......................... | 600/300 |
| 2006/0173260 A1* | 8/2006 | Gaoni et al. | .................. | 600/365 |

* cited by examiner

*Primary Examiner* — Sam Yao
*Assistant Examiner* — Bobby Soriano
(74) *Attorney, Agent, or Firm* — Eric P. Mirabel

(57) ABSTRACT

The Cellular GPRS system includes a cellular-based Glucometer (CBG) for blood glucose monitoring, a pedometer for exertion measurement, combined with user-entered dietary or other diabetes-relevant information. Data from all inputs is transmitted over a cellular network, using a GPRS or other wireless link. The data is preferably stored in the device prior to being transmitted wirelessly over the cellular airway to a central computer server. The remote computer server will evaluate the data received and respond with a data packet (making recommendations on further glucose measurement, exercise, diet, insulin requirements or other).

4 Claims, 2 Drawing Sheets

CELLULAR GPRS-COMMUNICATION LINKED GLUCOMETER—PEDOMETER

RELATED APPLICATIONS

This application claims priority to U.S. Provisional Application No. 61/046,881, filed Apr. 22, 2008.

BACKGROUND

In managing diabetes, it is well known that wellness is related to glucose level, and that blood glucose level is affected by exertion level (calories consumed) and diet. The calories consumed are related to the speed and force of movement and the mass of the subject. Walking uphill consumes more calories than downhill, or on a level, and running consumes more per unit time than walking. Existing pedometers do not account for vertical vs. horizontal acceleration, and require a particular orientation to differentiate these two axes to thereby determine steps taken and calorie expended (when the weight of the subject is known). This makes them difficult to use, and affects the accuracy of the results (if they are oriented wrongly and this is not detected).

Existing glucometers (which determines blood glucose level) and pedometers do not interact so as to correlate results from the glucometer with calories expended (based on the pedometer results). Such correlation can be used effectively to adjust the actions the subject takes, i.e., a low glucose level can be the result of exertion, and the subject could be instructed to reduce activity level rather than consuming carbohydrates.

One design of existing glucometers employs glucose dehydrogenase to generate electrons on a strip covered with blood, and the change in voltage across the strip is measured over time to determine glucose concentration. Resistance across the strip drops over time due to the chemistry of the strip and the increase in the product of the enzyme-catalyzed reaction. Measurement of the corresponding voltage drop is correlated with known blood glucose concentrations to determine the subject's blood glucose concentration.

The disadvantages of such glucometers include that they are noise sensitive, as voltage is calculated directly from the current flow. Noise-resistant designs are thus desirable.

There is also a need to measure exertion levels of the subject, then readily transmit data from glucometers and exertion measurement devices (e.g., pedometers) to a monitor, who can determine what instructions to provide the patient to maintain blood glucose at optimal levels. The transmission medium should be inexpensive and widely used, to avoid added costs.

SUMMARY

The Cellular GPRS system includes a cellular-based Glucometer (CBG) for blood glucose monitoring, a pedometer for exertion measurement, combined with user-entered dietary or other diabetes-relevant information. Data from all inputs is transmitted over a cellular network, using a GPRS or other wireless link. The data is preferably stored in the device prior to being transmitted wirelessly over the cellular airway (using a GPRS or other wireless communication link rather than a Bluetooth or voice-based link) to a central computer server. The remote computer server will evaluate the data received and respond with a data packet (making recommendations on further glucose measurement, exercise, diet, insulin requirements or other) which can be read on a cell phone or PDA or otherwise.

The glucometer design preferably involves a blood-glucose strip, where current across the strip, rather than voltage, is correlated with blood glucose levels. The pedometer design is most desirably a three-axis accelerometer, capable of determining and monitoring movement in any direction. This design allows the device to determine if the subject is walking or running.

Other data (particularly relating to diet and insulin use) can also be input and transmitted. The data as a whole can be evaluated at the central monitoring station, and specific recommendations to the patient (including, recommendations on insulin injection, need to eat carbohydrate, exercise level) can be readily made. These recommendations can be displayed on a cell phone or PDA, for immediate processing and action by the patient.

DESCRIPTION

The CBG electronics are preferably contained in a small housing that can easily be clipped to the shirt, pants, purse, or placed into a pocket. The electronics consist of a LCD display, cellular GPRS radio, glucometer, and accelerometer (used for the pedometer function). The CBG module is preferably powered by a rechargeable lithium ion battery so as to operate several days between charges.

The CBG pedometer can monitor activity of the user throughout the day. Along with information such as distance traveled, the pedometer can also access the effort expended during activity. The pedometer can differentiate between a brisk walk, run, long strides, or casual strolls. This information creates a more accurate assessment of calories expended during activity. Suitable pedometers are discussed below.

Figure 2:
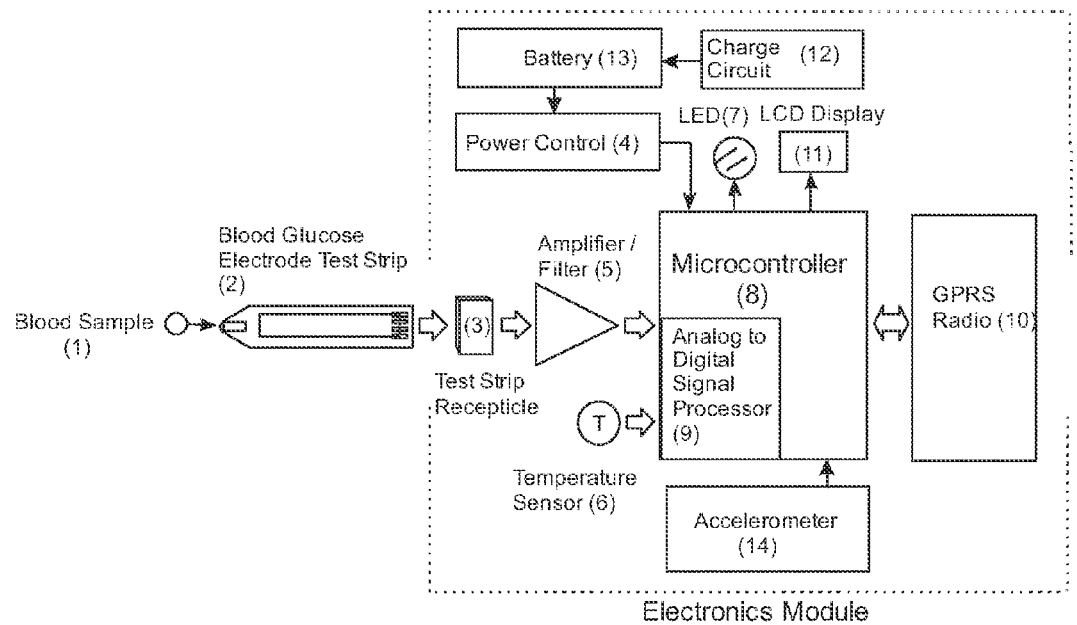
FIG. 2 is a block diagram of the functions of reading and analyzing a glucose test strip and transmitting the results through a GPRS.

Referring to FIG. 2, the glucometer is continuously powered and is continuously monitoring activity with the pedometer (14). Upon insertion of a blood glucose strip (2), it commences a blood glucose reading. In the glucometer of the invention, the current is not measured directly.

Using existing glucose monitoring strips, the glucometer requires 220 millivolts maintained across the two electrodes. One of the electrodes is a reference electrode and the other is the working electrode. The reference electrode is connected to electrical ground (common), and the working electrode is maintained at 220 mV. A microprocessor controlled voltage source (e.g., a Digital to Analog Converter—DAC), produces a voltage which is connected to the working electrode through a resistor of known value. A volt meter (e.g., an Analog to Digital Converter—ADC) is also connected to the working electrode to ensure that the 220 mV is always maintained.

When a blood sample is placed on the test strip, the resistance of the strip immediately drops, causing current flow. This causes the voltage on the working electrode to drop, which is sensed by the ADC and is immediately compensated for by the DAC. Over the next 10 seconds the resistance of the strip will first decrease for about 9 seconds, and thereafter, will increase causing the current flow to decrease. The ADC continuously monitors this change and signals the DAC to adjust the output voltage to maintain 220 mV on the working electrode.

During seconds 9 through 10, the calculated current values are averaged and this average is used to derive the actual blood glucose value. Because the voltage produced by the DAC is always known, the series resistance is known, and the working electrode voltage of 220 mV is known, the current through the strip can be accurately calculated. The blood glucose value is a direct function of the current flowing through the test strip and is adjusted for the ambient temperature during the test, and the strip manufacturing lot variance.

Figure 1:
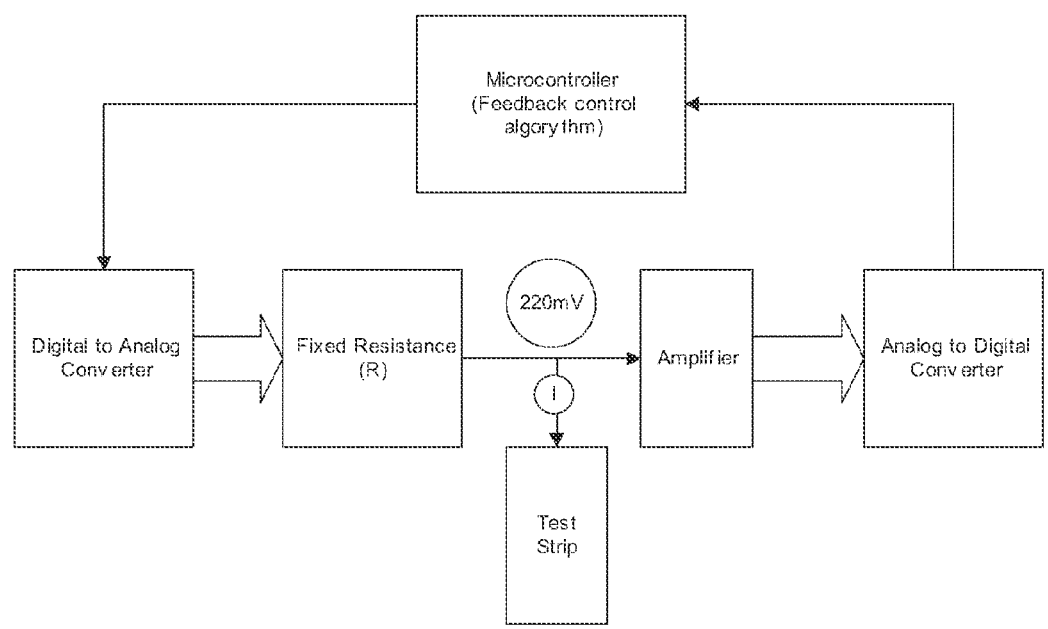
FIG. 1 is a block diagram of the functions of reading and analyzing a glucose test strip.

Referring to FIGS. 1 and 2, when a Blood Glucose Test Strip (2) is inserted into the Test Strip Receptacle (3), the Microcontroller (8) recognizes the insertion of the strip. The glucometer electronics performs the glucose strip reading function as depicted in FIG. 1:

1. Exactly 200 mV potential is produced across the working and reference electrodes of the strip,
2. When blood is applied to the strip, current begins to flow into the strip.
3. After 9 seconds an average of the current is calculated continuously until 10 seconds is reached,
4. The average current value directly correlates to the blood glucose level,
5. This value is further compensated for temperature variations and test strip production lot variations.
6. The microcontroller then executes the steps described above to accurately read the current flowing into the test strip. Over time, the resistance of the test strip continues to increase requiring the DAC to decrease its output,
7. Because the voltage output of the DAC is known, the fixed resistance is known, and the 220 mV reference is known, the current flowing into the test strip can be derived as:

$$I_{strip} = (V_{DAC} - V_{ref})/R$$

This measurement technique provides a very accurate high resolution current value with low noise, high repeatability, and a very wide dynamic current range without additional support electronics.

Once the Microcontroller (8) of FIG. 2 has confirmed that the blood sample has been acquired, the following occurs:

1. The digital representation of the Blood Glucose Test Strip (2) current is sampled and stored at regular intervals over a fixed period of time.
2. The slope of the current is noted. If the slope is trending in the wrong direction, the test is aborted with an error.
3. The Temperature Sensor (6) value is acquired by the Microcontroller (8) at regular intervals and is averaged over the entire test time.
4. A signal is sent to the Cellular GPRS (10) indicating that a test is in progress, which can in turn relay it to a central server.
5. The LED (7) begins to flash rapidly to indicate that a test is in progress.

At the completion of the test, the blood glucose value is determined as a function of the following:

1. The slope of the digital representation of the Blood Glucose Test Strip (2) sampled current verses time.
2. The average temperature during the test.
3. The test strip lot calibration value which is used to access a library stored within the Microcontroller (8) to compensate the calculated blood glucose value.
4. The LED (7) remains solid for 2 seconds and then turns off to indicate that the test is completed and that it is now safe to remove the test strip. The blood glucose value is shown on the LCD display.
5.

The final determined blood glucose value is then evaluated by the Microcontroller (8) to ascertain it is within an expected range or if the blood sample was actually a standard solution for test and verification. The results of the test are then sent to the GPRS (10) which in turn, relays this information to the server (11), for analysis.

If the GPRS link is not available, then the time of the blood glucose reading and the value of the reading are stored in the non-volatile memory of the glucometer. The memory can store up to 1000 readings. When the GPRS becomes available, the readings are then transferred to its memory.

The Microcontroller (8) enters into a low power sleep state and does not awaken until a new test strip is inserted, or is triggered to wake up from movement detected by the accelerometer.

FIG. 3 shows the separate operation of a three-axis pedometer, suitable for use as the accelerometer of FIG. 1. The device measures acceleration in three separate axes, and can measure human movement (walking, jogging, running) irrespective of orientation. By determining acceleration in multiple axes, and monitoring time, it can determine direction of movement. In walking/jogging/running, there is a vertical component of acceleration of shorter duration and with a different profile over time, than the acceleration component in the direction of travel. Also, in jogging or running, the vertical and direction of travel components have a different profile from walking, or from other motion (like driving a car). If there is no acceleration component input, the device goes into a power-saving sleep mode.

From the acceleration information, the distance traveled by the user is determined, and using this information, with the weight of the user, the energy expended (as calories) are determined, and then fed back to the microcontroller 8 (then to a GPRS and server) as shown in FIG. 2.

The microcontroller 8 is responsible for correlating data from the glucometer and pedometer. The results can be displayed on a cell phone (or an outside screen of a GPRS) and can be used a number of different ways, one of which is determining whether the correlated results are within or outside of a known index of such values. The index has been established based on the known relationship between exercise (consuming calories) and lowering blood glucose levels. Thus, for example, if the calories consumed over a given period correlate with a predicted drop in blood glucose, as long as the glucometer indicates that the level is within the index guidelines, no action by the user need be taken. But if the blood glucose level is outside the index guidelines, actions from "stop exercising" to "eat" or "take insulin" can be flashed on the display for the user to act on.

A related device which uses or relies on the various components described above is a combination glucometer adapter/pedometer, where the adapter can receive and decode input from a particular make/model (or several different makes/models) of glucometer. The results from the pedometer and the glucometer are still correlated and compared to the index, and displayed, as described above, Pedometer Function A 3 axis accelerometer (14) is used as the foundation for the pedometer function. The 3 axis accelerometer eliminates the need to orient the it to obtain an accurate reading. The microcontroller automatically determines the horizontal and vertical axis.

By using mathematical relationships between acceleration and time, distance traveled is calculated. Also calculated is the number of steps, pace, stride, effort (vertical acceleration), and calories expended (given body weight). The microcontroller acquires acceleration data from the accelerometer every 100 mS. This data is processed and averaged and send to the GPRS for transmission.

Power Management

The glucometer and pedometer are powered from a lithium ion battery which is rechargeable. This battery technology does not exhibit "memory effect" which is ideal for long run times. The charge circuit (12) will bring the battery to a full charge in less than 5 hours for a completely discharged battery. Typically the charge time is around 2 hours. The Glucometer or pedometer can also be charged from a standard mini-USB connector which can be plugged into a computer (or any USB power source) for power or a wall transformer. The run time between charges on average is about 1 week.

The glucometer and pedometer should always be powered. To conserve power, they operate at different levels of power conservation depending upon the activity as follows:

1. Active Mode:
a. The glucometer and pedometer have an active GPRS radio link is actively transmitting data.
b. A cell phone can request that data is sent via the GPRS radio,
c. The accelerometer is checked for motion.
2. Sleep Mode:
a. The GPRS radio is in a low power listening mode but is not communicating.
b. The accelerometer is accessed every 100 mS detecting motion,
3. Deep Sleep Mode:
a. The GPRS radio is in sleep mode,
b. The accelerometer is accessed every minute due to minimal motion.
4. Hibernate:
a. The GPRS radio is in sleep mode.
b. The accelerometer is accessed every 10 minutes due to no movement detected for 5 minutes while in the Sleep Mode. The glucometer progresses to the Active mode once the accelerometer detects motion or a blood glucose reading has been taken. As glucose or movement activities decrease, the "Device" descends into the deeper modes of sleep to retain power.

It should be understood that the terms and expression and examples used herein are exemplary only, and not limiting, and that the scope of the invention is defined only in the claims which follow and includes all equivalents of the subject matter of those claims.

What is claimed is:

1. A method of controlling diabetes comprising:
  determining blood glucose level in a sample using an assay which indicates blood glucose level based on a predetermined and temperature-adjusted change in current flow through a support which has contacted sample blood;
  determining exertion level based on detection of motion patterns from a device which: (i) measures acceleration in three separate axes and, (ii) based on the acceleration patterns from the three axes, said device distinguishes the motions associated with walking from jogging from riding in a vehicle;
  continuously transmitting the blood glucose level and exertion level to a monitor for analysis over a cellular GPRS link; and
  receiving back recommendations from the monitor.

2. The method of claim 1 further including acting on the recommendations by one or more of:
  performing another blood glucose level assay;
  increasing or decreasing exertion level;
  injecting insulin; or
  eating carbohydrates.

3. The method of claim 1 wherein the monitor is a computer server or a health professional.

4. The method of claim 1 wherein the patient enters information about the food(s) recently consumed.

* * * * *